(12) United States Patent
Liu

(10) Patent No.: US 12,102,459 B2
(45) Date of Patent: Oct. 1, 2024

(54) GENERAL PET DEVICE WITH GRADUALLY NARROWED HEAD

(71) Applicant: SHANDONG MADIC TECHNOLOGY CO., LTD., Linyi (CN)

(72) Inventor: Jiguo Liu, Linyi (CN)

(73) Assignee: SHANDONG MADIC TECHNOLOGY CO., LTD., Linyi (CN)

( * ) Notice: Subject to any disclaimer, the term of this patent is extended or adjusted under 35 U.S.C. 154(b) by 294 days.

(21) Appl. No.: 17/767,242

(22) PCT Filed: Oct. 23, 2019

(86) PCT No.: PCT/CN2019/112763
§ 371 (c)(1),
(2) Date: Apr. 7, 2022

(87) PCT Pub. No.: WO2021/068288
PCT Pub. Date: Apr. 15, 2021

(65) Prior Publication Data
US 2022/0370022 A1    Nov. 24, 2022

(30) Foreign Application Priority Data

Oct. 9, 2019 (CN) .......................... 201910955892.3

(51) Int. Cl.
*A61B 6/03* (2006.01)
*G01T 1/164* (2006.01)
(Continued)

(52) U.S. Cl.
CPC ............ *A61B 6/037* (2013.01); *G01T 1/1644* (2013.01); *G01T 1/2023* (2013.01); *G01T 1/2985* (2013.01)

(58) Field of Classification Search
CPC ..... A61B 6/037; G01T 1/1644; G01T 1/2023; G01T 1/2985
See application file for complete search history.

(56) References Cited

U.S. PATENT DOCUMENTS 7,180,074 B1 * 2/2007 Crosetto ............... G01T 1/1615
250/370.09
2015/0378035 A1   12/2015 Choi et al.
(Continued)

FOREIGN PATENT DOCUMENTS

| CN | 102362198 A | 2/2012 |
| CN | 109846503 A | 6/2019 |
| CN | 109846504 A | 6/2019 |

OTHER PUBLICATIONS

International Search Report dated May 27, 2020 received in International Application No. PCT/CN2019/112763 together with an English language translation.

*Primary Examiner* — Christine S. Kim
(74) *Attorney, Agent, or Firm* — Scully, Scott, Murphy & Presser, P.C.

(57) ABSTRACT

Disclosed is a general PET device (1) with a gradually narrowed head, the device comprising a body (2), a head (3) and a top (4) closely arranged in sequence, wherein the body (2) is composed of a plurality of body module rings (21); the head (3) is composed of N head module rings (31), with N being a natural number and being at least two; the top (4) is composed of a plurality of top PET detection modules (41); each of the body module rings (21) is composed of several body PET detection modules (22) evenly distributed in a circumferential direction thereof, and all the body module rings (21) are closely arranged in an axial direction to form the body (2); in the N head module rings (31), the rings sequentially decreases in size, and are closely arranged in the axial direction in a sequence from the first head module (Continued)

ring (31) to the Nth head module ring (31); and the detection surfaces of the plurality of top PET detection modules (41) are located in the same plane, and all the detection surfaces face the head (3) or the body (2).

11 Claims, 3 Drawing Sheets

(51) Int. Cl.
*G01T 1/202* (2006.01)
*G01T 1/29* (2006.01)

(56) References Cited

U.S. PATENT DOCUMENTS

2017/0123084 A1* 5/2017 Ferenc ................ G01T 1/20188
2019/0053772 A1 2/2019 Baviera et al.

* cited by examiner

GENERAL PET DEVICE WITH GRADUALLY NARROWED HEAD

TECHNICAL FIELD

The present disclosure belongs to the field of radiographic medical imaging apparatus, and relates to a whole-body PET device with a gradually narrowed head.

BACKGROUND

Positron emission tomography (hereinafter referred to as PET) apparatuses are widely used for specific imaging of animals and human body (hereinafter referred to as scanned object). In PET imaging, it is necessary to first inject a positron nuclide-labeled tracer into the scanned object, and then image the distribution of the tracer in the scanned object. The imaging specificity of the site labeled by the tracer is strong, and dynamic imaging can be realized with a high degree of recognition.

An axial depth of a detector of the traditional PET apparatus is insufficient, and only a relatively limited local part can be scanned at a time. If it is desired to obtain a PET image of the whole human body, locally scanned images of multiple (such as 8 to 10) beds have to be spliced to obtain an image of the whole body. The imaging speed of this imaging method is slow, each bed takes 1-5 minutes, and an axial field of view is about 20 cm. One whole-body imaging requires 8-10 beds and takes at least 8 minutes, and additional computing time is required. Moreover, it is impossible to splice the images obtained from different beds to obtain dynamic information of the whole body, and the dynamic information of the whole body cannot be obtained directly from the PET apparatuses at individual beds.

For special cases, in order to obtain the situation of systemic drug metabolism, the axial field of view of the PET apparatus has been extended in the prior art. When a length/depth of the axial field of view exceeds or approaches the length of the scanned object, whole-body dynamic imaging can be performed on the scanned object. For example, in Sci. Transl. Med, vol. 9, eaaf6169 (2017) 15 Mar. 2017, Cherry et al., by axially extending a detector ring of human body PET to 2 meters, it is possible to perform whole-body dynamic imaging on the human body. However, the size of the detector ring of the PET of these whole-body imaging apparatuses is exactly consistent in the entire axial direction, and only the length/depth of the detector is extended in the axial direction. The problem with this design of detector ring is that the sensitivity in the scanning field of view is not uniform enough. The sensitivity is the highest in an overall middle part of the detector. As the position shifts from a center to two ends of the detector along an axis, the sensitivity decreases rapidly, and drops to a very low level (even zero) at the positions of the two ends of the detector. FIG. 2 shows the extended PET apparatus in the prior art.

The reason for this phenomenon is that PET adopts a data acquisition method of coincidence detection. When two gamma rays of 511 keV are simultaneously detected on two detector crystals just opposite to each other, it is called a true coincidence event. Only in this situation will the two gamma rays be taken as an effective positron event. An occurrence position of this positron event lies on a straight line between the two crystals, which is the part desired to be detected. This straight line is called line of reaction, hereinafter referred to as LOR.

For the comparison between the position at the center of the axial field of view of the detector and the position not at the center of the axial field of view but at an edge, the probability of detecting LORs occurring from different positions differs greatly due to the difference in position. Most of the LORs occurring from the center position can be detected as long as they are not horizontal or nearly horizontal, but for LORs occurring from the edge position, only some of them that are perpendicular to or nearly perpendicular to the axial direction can be detected, which therefore leads to a situation in which as the occurrence position deviates from the center of LOR, that is, as it is closer to the edge position of the detector, the sensitivity becomes lower.

In the applicant's previous application CN109846504A, a full-angle coinciding PET detector is provided, which consists of a barrel portion in the middle and concave curved end caps at both ends. As compared with the barrel-type detector that is only elongated, the enclosed solid space angle is further increased, and the sensitivity is further improved. However, for this capsule-like PET detector, the concave curved end caps at both ends make it difficult to support the detector. Since the placement angle and position of each detector must be calculated according to the design of curved surface, complicated angle arrangements are required in the design, and a five-axis apparatus is also required to manufacture the support device. The cost is high and the steps are cumbersome, which not only makes it difficult to design and install, but also brings difficulty to later maintenance.

In view of the above problems, if an apparatus with a very high overall solid space angle and a detection sensitivity also comparable to the above-mentioned capsule-type PET detector can be provided, but the apparatus does not require a five-axis apparatus in design and installation, and does not require cumbersome and complicated angle correction, then the production efficiency will be greatly improved and the detection effect will not be affected.

SUMMARY

In view of the above problems in the prior art that the capsule-type PET detector requires a five-axis apparatus during design and installation, and requires cumbersome and complicated angle setting and correction, an alternative arrangement to the capsule-type PET apparatus is presented. At an end, a gradually narrowed head formed by several rings that are closely fitted and a planar top are used to replace a curved surface-like end, which greatly reduces the difficulty in production and design of the apparatus without reducing the overall solid space angle and sensitivity, and which also makes the installation and maintenance easier and more convenient.

The present disclosure claims a whole-body PET device with a gradually narrowed head, which includes a body, a head and a top that are closely arranged in sequence. The body is composed of a plurality of body module rings, the head is composed of N head module rings, and the top is composed of a plurality of top PET detection modules; where N is a natural number and the number is at least 2; each of the body module rings is composed of several body PET detection modules evenly distributed in a circumferential direction, and a detection surface of each body PET detection module is arranged facing an interior of the body; all the body module rings are closely arranged in an axial direction to form the body; among the N head module rings, a size of the rings decreases in sequence from a first head module ring to a $N^{th}$ head module ring, and the N head module rings are closely arranged in the axial direction in the order from the first head module ring to the $N^{th}$ head module ring to form the head; each of the N head module rings is composed of several head PET detection modules; detection surfaces of the plurality of top PET detection modules are located in the same plane or approximately in the same plane, and the detection surfaces of all the top PET detection modules are oriented in a direction toward the head or the body.

Preferably, the number of N is one of the integers of 2-5; the number of PET detection modules on the $N^{th}$ head module ring is 1-5 smaller than the number of PET detection modules on a $(N-1)^{th}$ head module ring; the number of PET detection modules on the first head module ring is 1-5 smaller than the number of PET detection modules on the body module ring; and at least 85% of the area of an outer opening portion of the $N^{th}$ head module ring is covered by the top.

Preferably, the number of N is 2; the number of head PET detection modules on a second head module ring is 1-2 smaller than the number of head PET detection modules on the first head module ring; the number of PET detection modules on the first head module ring is 1-2 smaller than the PET detection modules on the body module ring; and at least 90% of the area of the outer opening portion of the $N^{th}$ head module ring is covered by the top.

Preferably, the PET device further includes a tail, and the tail is composed of a plurality of tail PET detection modules; detection surfaces of the plurality of tail PET detection modules are located in the same plane or approximately in the same plane, and the detection surfaces of all the tail PET detection modules are oriented in a direction toward the head or the body.

Preferably, the installation of the body is implemented using a first support method or a second support method. In the first support method, the body is installed between a left body support plate and a right body support plate, and a body guide column frame is installed between the left body support plate and the right body support plate; for the body guide column frame, several lateral horizontal guide columns and approximately circular guide columns connected end to end in a vertical plane are arranged cross each other to form an overall hollow cylindrical body guide column frame and several inter-column positions suitable for installation of body PET modules, and each body PET detection module is installed in the inter-column position. In the second support method, the body is installed between a left body support plate and a right body support plate, and a body guide column frame is installed between the left body support plate and the right body support plate; for the body guide column frame, several lateral horizontal guide columns and approximately circular guide column loops connected end to end in a vertical plane are arranged cross each other to form an overall hollow cylindrical body guide column frame and several inter-column positions suitable for installation of body PET modules, and each body PET detection module is installed in the inter-column position; and at least one of the above guide column loops is replaced by a body intermediate support plate.

Preferably, the installation of the head is implemented using a third support method or a fourth support method. In the third support method, the head is installed between a left head support plate and a right head support plate; the first head module ring is installed between the left head support plate and a first head intermediate support plate, a $M^{th}$ head module ring is installed between a $(M-1)^{th}$ head intermediate support plate and a $M^{th}$ head intermediate support plate, where $2 \leq M \leq N-1$ and M is an integer, and the $N^{th}$ head module ring is installed between a $(N-1)^{th}$ head intermediate support plate and the right head support plate; each head PET detection module is installed on two adjacent head guide columns, and each of the head guide columns is parallel to an axis of the head. In the fourth support method, a right side of a $M^{th}$ head module ring is perpendicularly installed on a $M^{th}$ head intermediate support plate, where $1 \leq M \leq N-1$ and M is an integer, and a left side of the $N^{th}$ head module ring is installed on a $(N-1)^{th}$ head intermediate support plate; each head PET detection module is installed on two adjacent head guide columns, and each of the head guide columns is parallel to an axis of the head.

Preferably, the installation of the top is implemented using a fifth support method or a sixth support method. In the fifth support method, the top is fixed on one surface of a vertically arranged top support plate. In the sixth support method, the top is fixed on a second plate, and the second plate is embedded with a nut seat which cooperates with a lead screw driven by a motor, so that the top can be moved in parallel when driven by the motor. Except for the top support plate, all the other support plates have circular or approximately circular through holes.

Preferably, both the left body support plate and the right body support plate have a bottom support portion, and the body intermediate support plates have a bottom support portion, or are supported by several support columns penetrating the left body support plate, the right body support plate and all the body intermediate support plates.

Preferably, both the left head support plate and the right head support plate have a bottom support portion, and the head intermediate support plates have a bottom support portion, or are supported by several support columns penetrating the left head support plate, the right head support plate and all the head intermediate support plates.

Preferably, the top support plate has a bottom support portion, and a shaft bushing of the motor is embedded and fixed on a first plate.

Preferably, the body PET detection modules, the head PET detection modules and the top PET detection modules are all PET detection modules of uniform specifications, and all have a square or rectangular detection surface; and each PET detection module is composed of a PET detection crystal, a light guide and a photosensor array arranged in sequence. A coincidence circuit is connected between every two PET detection modules; a material of the PET detection crystal is a scintillation crystal, and the scintillation crystal consists of a crystal strip array composed of a plurality of crystal strips or consists of one or more integrally cut crystal. Each PET detection module is specifically configured such that the light guide is tightly coupled to both the photosensor array and the PET detection crystal.

Preferably, the material of the scintillation crystal is selected from one or more of bismuth germanate (BGO) crystal, sodium iodide (NaI) crystal, NaI (Tl) single crystal, lutetium silicate (LSO) crystal, gadolinium silicate (GSO) crystal and yttrium lutetium silicate (LYSO). A spacer made of a high atomic number material is installed between all the detection module rings, or a spacer made of a high atomic number material is installed between some of the detection module rings; the high atomic number material is lead or tungsten. The crystal strip array is composed of a plurality of crystal strips; and each of the one or more crystal blocks is composed of one or more integrally cut crystal.

Preferably, it includes the aforementioned whole-body PET device with a gradually narrowed head, and further includes a bottom; the bottom, the body, the head and the top are closely arranged in sequence; and the bottom is composed of a plurality of bottom PET detection modules.

Detection surfaces of the plurality of bottom PET detection modules are located in the same plane or approximately in the same plane, the bottom is located on the other side of the body opposite to the head, and the bottom can move under the action of a mechanical device to avoid an opening of the body.

Preferably, it includes the aforementioned whole-body PET device with a gradually narrowed head, and further includes a bottom and a tail; the bottom is composed of a plurality of bottom PET detection modules, and the tail is composed of M tail module rings, where M is a natural number and the number is at least 2. Among the M tail module rings, a size of the rings decreases in sequence from a first tail module ring to a $M^{th}$ tail module ring, and the M tail module rings are closely arranged in the axial direction in the order from the first tail module ring to the $M^{th}$ tail module ring to form the tail. Detection surfaces of the plurality of bottom PET detection modules are located in the same plane or approximately in the same plane, and the bottom is located on the other side of the body opposite to the head; the bottom and the tail are integrally fixed, and can move under the action of a mechanical device to avoid an opening of the body.

Preferably, it includes the aforementioned whole-body PET device with a gradually narrowed head, and further includes a second whole-body PET device arranged mirror-symmetrical with the whole-body PET device; the whole-body PET device has a second body, a second head and a second top that are mirror-symmetrical with the body, the head and the top respectively; the second body, the second head and the second top are closely arranged in sequence, and an opening of the body and a second opening of the second body can move within a range of 10 cm.

The advantages of the present disclosure are presented as follows. (1): The manufacturing is easy. The top detector is a planar detector, and the body and the head are common cylindrical detectors with mere difference in the size. When they are combined together, the manufacturing and design processes are not very complicated, and are easy to implement, but a similar effect to the capsule-type whole-body PET device can also be achieved, and the design and manufacturing difficulty is significantly lower than that of a complicated device that requires a five-axis apparatus for manufacturing. (2): The design and installation are simple. For a capsule-type detector, such as that shown in CN109846504A, although the solid space angle has almost reached a maximum value, most of the detection modules have irregular angles, which are specific values that need to be designed and calculated separately, thus making it difficult to design, install and maintain, and leading to a complicated process; by contrast, the gradually narrowing design of the present application, although actually covering a slightly smaller solid space angle, that is, the adjoining position of the body and the head as well as some areas between the head PET module rings are not covered, the overall loss of the solid space angle is at most 8%-13% that of the capsule type, but the overall sensitivity is still in a high state. The quality of obtained static or dynamic whole-body images is not significantly reduced, and the advantage is that the design, installation and maintenance thereof are very simple. (3): In view of the actual situation that the head of the detection object is slightly smaller than the body, by designing a gradually narrowed head and a top much smaller than the opening of the body, the whole-body detection is realized while ensuring the passability, and the number of detection modules actually in use is significantly smaller than that of general whole-body apparatuses. Since the cost of detection crystals is high, a better detection effect is ensured while saving the cost.

BRIEF DESCRIPTION OF THE DRAWINGS

In order to illustrate the embodiments of the present disclosure or the technical solutions in the prior art more clearly, the accompanying drawings that are required to be used in describing the embodiments or the prior art will be introduced briefly in the following. Obviously, the drawings in the following description only illustrate some embodiments of the present disclosure. For those skilled in the art, other drawings can also be obtained according to these drawings without creative efforts.

Components corresponding to reference signs: 1: whole-body PET device; 2: body; 3: head; 4: top; 21: body module ring; 22: body PET detection module; 23: left body support frame; 24: right body support frame; 25: body guide column frame; 26: inter-column position; 27: body intermediate support plate; 28: support column; 31: head module ring; 32: head PET detection module; 33: head intermediate support plate; 34: head guide column; 41: top PET detection module; 42: synchronous pulley; 43: synchronous belt; 44: motor; 45: motor bushing; 461: first plate; 462: second plate; 463: front support column; 464: rear support column; 465: rear lead screw; 5: guide column; 6: support wing; 7: insulating ring; 8: bottom plate.

DETAILED DESCRIPTION

Preferred embodiments of the present disclosure will be described in detail below with reference to the accompanying drawings, so that the advantages and features of the present disclosure can be more easily understood by those skilled in the art, and the scope of protection of the present disclosure can be more clearly defined.

Figure 1:
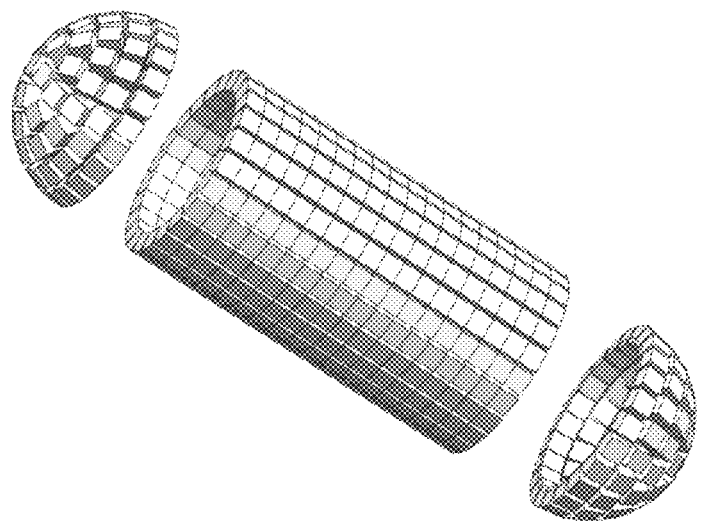
FIG. 1 shows a whole-body PET apparatus in the prior art.

FIG. 1 shows a capsule-type whole-body PET detection apparatus shown in CN109846504A, which is divided into a barrel portion in the middle and hemispherical detection portions at both ends, and which realizes the theoretical maximum solid space angle of whole-body PET detection. The sensitivity is also extremely high. However, due to the complexity of angle distribution, the design, installation and maintenance of the two ends are extremely difficult. The present application is an improvement proposed on this basis.

First Embodiment

In this embodiment, an overall arrangement of detectors of a whole-body PET device with a gradually narrowed head will be described, and a variation range in its implementation will be specifically described.

A whole-body PET device with a gradually narrowed head includes a body, a head and a top which are closely arranged in sequence. Herein, the body is a hollow cylindrical detection portion, and an inner side face thereof is a detection surface. The way in which the body cooperates with the head and the top is unique to the present disclosure.

If the cylindrical body is used to cooperate with a larger top, the whole-body detection can also be realized, but the number of detection modules actually used is much larger.

The body is composed of a plurality of body module rings, the head is composed of N head module rings, and the top is composed of a plurality of top PET detection modules, where N is a natural number and the number is at least 2. Herein, N is at least 2, so as to make the effect of saving detection modules for the apparatus obvious enough. If there is only one head module ring, the effect is not obvious. When N is at least 2, a rightmost module ring of the body to a $N^{th}$ head module ring can form a stepwise narrowed head, so that the head of a detection object or a detection phantom can be detected, and it is significantly cheaper than the method without the narrowed arrangement. Correspondingly, since an opening of the $N^{th}$ head module ring is greatly reduced, the number of detection modules required for the top is also greatly reduced.

Each of the body module rings is composed of several body PET detection modules evenly distributed in a circumferential direction, and a detection surface of each body PET detection module is arranged facing an interior of the body; all the body module rings are closely arranged in an axial direction to form the body. All the specifications of the body module rings are the same. When a span of several consecutive body module rings is not large, the body module rings are fixed by a ring formed by guide columns. If the span is large, support plates are arranged between the body module rings for fixing. For the requirement of passability, the support plates need to be provided with large circular through holes.

Among the N head module rings, a size of the rings decreases in sequence from a first head module ring to a $N^{th}$ head module ring, and the N head module rings are closely arranged in an axial direction in the order from the first head module ring to the $N^{th}$ head module ring to form the head; each of the N head module rings is composed of several head PET detection modules. In fact, the head module ring is similar to the body module ring in configuration, except that there are fewer detection modules on the head module ring. The first head module ring has fewer detection modules than the body module ring, and the $N^{th}$ head module ring has fewer detection modules than the $(N-1)^{th}$ head module ring.

Detection surfaces of the plurality of top PET detection modules are located in the same plane or approximately in the same plane, and the detection surfaces of all the top PET detection modules are oriented in a direction toward the head or the body. By "located in the same plane", it means that all the detection surfaces are located in the same vertical plane. By "approximately located in the same plane", it means that the detection surfaces of the top may be slightly convex inward or slightly concave outward due to the actual requirement of detection sensitivity.

Preferably, the PET device further includes a tail, and the tail is composed of a plurality of tail PET detection modules; detection surfaces of the plurality of tail PET detection modules are located in the same plane or approximately in the same plane, and the detection surfaces of all the tail PET detection modules are oriented in a direction toward the head or the body. Generally speaking, PET images do not care too much about the feet, but a tail may also be added to the above device when needed. The tail covers an opening at a distal end of the body when the detection object or phantom enters the device, thus enabling full-angle coverage of PET detection, which is the same as the capsule-type apparatus.

Second Embodiment

In the whole-body PET device with a gradually narrowed head described in the first embodiment, the number of N is one of the integers of 2-5; herein, mainly for the consideration of a general length of the head, the number of N is different. For example, due to the different sizes of the detection modules, the head can be designed to have 5 stages when the size is small, and when the size is large, designing the head to have 2 stages would be enough.

The number of PET detection modules on the $N^{th}$ head module ring is 1-5 smaller than the number of PET detection modules on the $(N-1)^{th}$ head module ring; and the number of PET detection modules on the first head module ring is 1-5 smaller than the number of PET detection modules on the body module ring. The decreasing number of the head module rings of each stage is mainly caused by the different sizes of the detection modules. When the detection module is large, one module fewer already means an obvious reduction in the size. When the size of the detection module is small, the number of missing modules in each stage may reach 5. Of course, due to the actual accommodation requirement on the head, the number of modules actually reduced in the head module ring of each stage may not be regular.

At least 85% of the area of an outer opening portion of the $N^{th}$ head module ring is covered by the top. When at least 85% of the area of the opening portion is covered by the top, general detection requirements can be met, and the detection modules of the top will not be wasted. Preferably, 95%-100% of the area of the opening portion is covered by the top. When 100% of the area of the opening portion is covered by the top, the solid space angle of the device reaches the highest.

It should be noted that the above first and second embodiments are full descriptions of preferred implementations, and third to fifth embodiments are specific descriptions, not specific limitations to the content of the present disclosure. The third to fifth embodiments are only specific examples.

Third Embodiment

Figure 2:
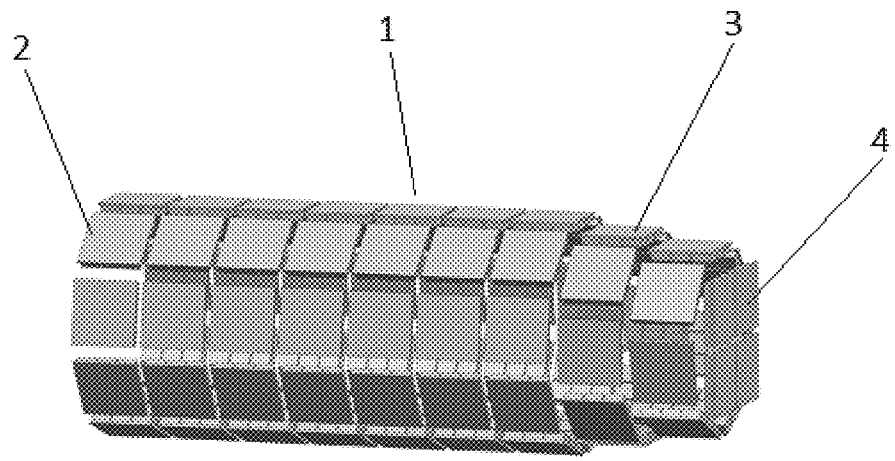
FIG. 2 is a general view of the whole-body PET device.
Figure 3:
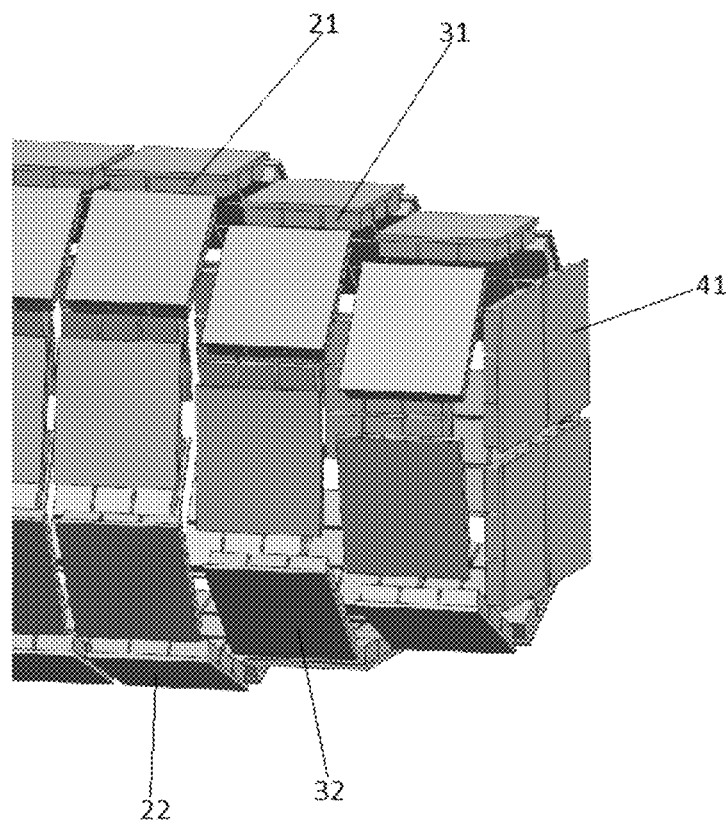
FIG. 3 is a schematic view of specific components of a body, a head and a top.

Specifically, the number of N is 2. As shown in FIG. 2, there are two head module rings, i.e., a first head module ring and a second head module ring. The number of head PET detection modules on the second head module ring is one smaller than the number of head PET detection modules on the first head module ring; the number of PET detection modules on the first head module ring is one smaller than the number of PET detection modules on the body module ring; and the number of the body module rings is 7.

There are 9 modules on one body module ring, 8 modules on the first head module ring, and 7 modules on the second head module ring. The top is formed by splicing 4 modules with vertically inwardly facing detection surfaces in an array of 2*2.

95%-96% of the area of the outer opening portion of the second head module ring is covered by the top. The specifications of all the modules are uniform, and the detection surfaces are square.

Fourth Embodiment

Specifically, the number of N is 2. There are two head module rings, i.e., a first head module ring and a second head module ring. The number of head PET detection modules on the second head module ring is two smaller than the number of head PET detection modules on the first head module ring; the number of PET detection modules on the first head module ring is two smaller than the number of PET detection modules on the body module ring; and the number of the body module rings is 10.

There are 13 modules on one body module ring, 11 modules on the first head module ring, and 9 modules on the second head module ring. The top is formed by splicing 9 modules with vertically inwardly facing detection surfaces in an array of 3*3.

93%-94% of the area of the outer opening portion of the second head module ring is covered by the top.

The specifications of all the modules are uniform, and the detection surfaces are square. The area is uniformly about half of the detection surface area in the third embodiment.

Fifth Embodiment

Specifically, the number of N is 3. There are three head module rings, i.e., a first head module ring, a second head module ring and a third head module ring. The number of head PET detection modules on the second head module ring is three smaller than the number of head PET detection modules on the first head module ring, and the number of head PET detection modules on the third head module ring is three smaller than the number of head PET detection modules on the second head module ring; the number of PET detection modules on the first head module ring is three smaller than the number of PET detection modules on the body module ring; and the number of the body module rings is 12.

There are 19 modules on one body module ring, 16 modules on the first head module ring, 13 modules on the second head module ring, and 10 modules on the third head module ring. The top is formed by splicing 16 modules with vertically inwardly facing detection surfaces in an array of 4*4.

92%-93% of the area of the outer opening portion of the second head module ring is covered by the top.

The specifications of all the modules are uniform, and the detection surfaces are square. The area is uniformly about ⅓ of the detection surface area in the third embodiment.

Sixth Embodiment

In this embodiment, the installation methods of the body, the head and the top are mainly described. The installation of the body is implemented using a first support method or a second support method.

In the first support method, the body is supported by a left body support plate and a right body support plate at both ends and a hollow cylindrical body guide column frame. In the first support method, the body is installed between the left body support plate and the right body support plate, and the body guide column frame is installed between the left body support plate and the right body support plate; for the body guide column frame, several lateral horizontal guide columns and approximately circular guide columns connected end to end in a vertical plane are arranged cross each other to form the overall hollow cylindrical body guide column frame and several inter-column positions suitable for the installation of the body PET modules; the inter-column positions are slightly larger than the detection modules, and each body PET detection module is installed in the inter-column position. Each detection module is installed on the guide columns around it through a plurality of insulating rings or insulating parts. Each of the lateral horizontal guide columns is horizontal, and the lateral horizontal guide columns with overlapping projections viewed from the side are connected end to end to form a long column. The approximately circular guide columns connected end to end in the vertical plane form a guide column loop.

In the second support method, for the body guide column frame, several lateral horizontal guide columns and approximately circular guide column loops connected end to end in a vertical plane are arranged cross each other. The main arrangement is the same as the first support method. The difference from the first support method is that at least one of the aforementioned guide column loops is replaced by a body intermediate support plate. By "at least one" herein, it may mean that only one of the guide column loops or all the guide column loops may be replaced by the intermediate support plate(s). Since the body module rings need to be kept stable, in the most stable case, there can be no guide column loops provided, and all of them are replaced by the intermediate support plates; that is, each body module ring is actually fixed by the support plates on both sides and a loop of guide columns parallel to each other.

The left body support plate and the right body support plate each have a bottom support portion, which is necessarily required.

In fact, considering the convenience of disassembly and assembly as well as the need for support, it is generally not necessary to use the intermediate support plates for all the body module rings. As an example, in a case where there are 6 sets of body module rings, for example, two intermediate support plates are provided between the second set and the third set, as well as between the fourth set and the fifth set, or one intermediate support plate is provided between the third set and the fourth set, which can meet the needs.

In a case where the intermediate support plate is provided, in order to reinforce the intermediate support plate, the body intermediate support plate can be reinforced in two ways. In a first way, similar to the shape of the left body support plate and the right body support plate, the body intermediate support plate is provided with a bottom support portion. In a second way, the body intermediate support plates are supported by several support columns penetrating the left body support plate, the right body support plate and all the body intermediate support plates. The support column is horizontal, and if there are several support columns, they are evenly distributed.

The installation of the head is implemented using a third support method or a fourth support method.

In the third support method, separate left head support plate and right head support plate are provided at both ends, and the head is installed between the left head support plate and the right head support plate; the first head module ring is installed between the left head support plate and a first head intermediate support plate, a $M^{th}$ head module ring is installed between a $(M-1)^{th}$ head intermediate support plate and a $M^{th}$ head intermediate support plate, where $2≤M≤N-1$ and M is an integer, and the $N^{th}$ head module ring is installed between a $(N-1)^{th}$ head intermediate support plate and the right head support plate; each head PET detection module is installed on two adjacent head guide columns, and each of the head guide columns is parallel to an axis of the head.

In the above third support method, each head module ring is located between two adjacent support plates, which ensures the stability of each detection module of the head.

Due to the different sizes of the head module rings of each stage, it is generally inconvenient for two adjacent head module rings to be connected by the loop of guide columns, but it is also possible to use a combination of two guide column loops of different sizes to transition. In this combination, two guide column loops of different sizes are located in the same vertical plane and are connected by some other guide columns.

The fourth support method is different from the third support method in that the left head support plate and the right head support plate are not provided. On the premise that the intermediate support plate is not missing, the head can also be stabilized, and the head can also better fit with the body and the top after the support plates at both ends are removed.

Preferably, the installation of the top is implemented using a fifth support method or a sixth support method. In the fifth support method, the top is fixed on one surface of a vertically arranged top support plate. In the sixth support method, the top is fixed on a second plate, and the second plate is embedded with a nut seat which cooperates with a lead screw driven by a motor, so that the top can be moved in parallel when driven by the motor. Except for the top support plate, all the other support plates have circular or approximately circular through holes.

The fifth support method is suitable for a situation in which the top does not need to be moved, and can have a better fixing effect.

In the sixth support method, the top can be translated left and right or up and down, which can meet the needs of actual detection.

Specifically, both the left body support plate and the right body support plate have a bottom support portion, and the body intermediate support plate has a bottom support portion, or is supported by several support columns penetrating the left body support plate, the right body support plate and all the body intermediate support plates.

Specifically, both the left head support plate and the right head support plate have a bottom support portion, and the head intermediate support plate has a bottom support portion, or is supported by several support columns penetrating the left head support plate, the right head support plate and all the head intermediate support plates.

Preferably, the top support plate has a bottom support portion, and a shaft bushing of the motor is embedded and fixed on a first plate.

In fact, if consideration is only given to detection, it is not necessary for the top to be movable, but for the need to reduce the claustrophobic feeling of the detection object, or for the needs of service, maintenance and replacement, the top can be made movable.

In fact, the left body support plate and the right body support plate at least have a bottom support portion, and the left head support plate and the right head support plate also at least have a bottom support portion, which can ensure the stability of the device. Since the right body support plate adjoins the left head support plate, they can be one support plate. All the intermediate support plates may have a bottom support portion.

Seventh Embodiment

In this embodiment, in order to explain the support method in the sixth embodiment, an example of a specific support method is given.

Figure 4:
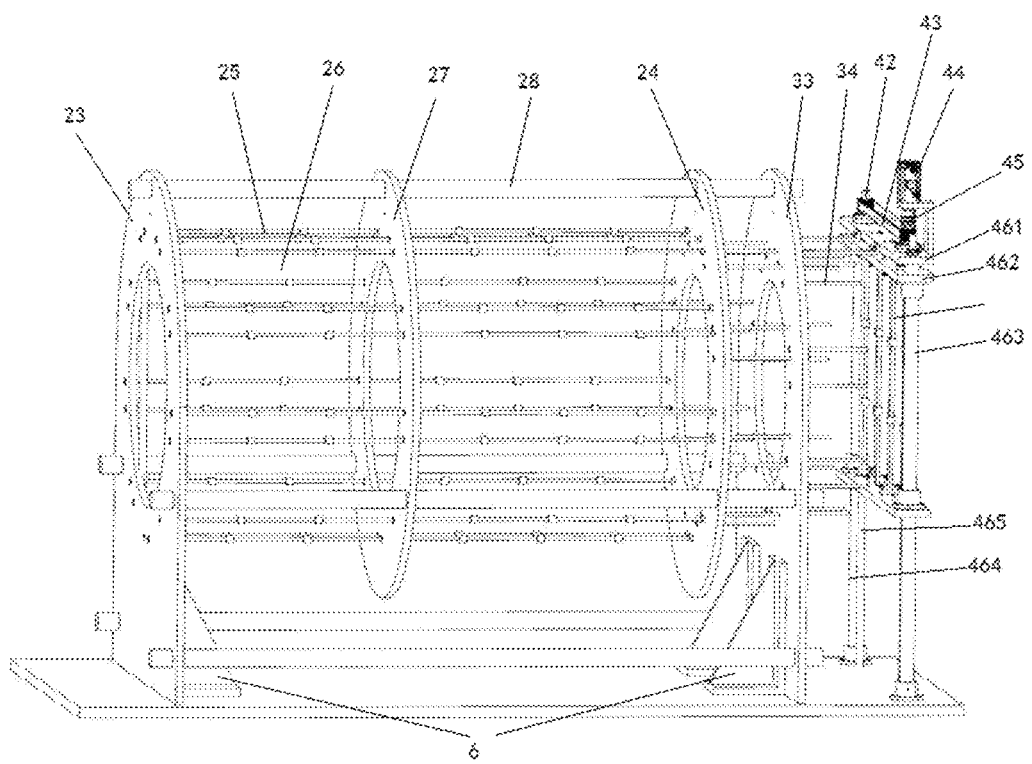
FIG. 4 is a specific configuration view of the apparatus without modules installed.
Figure 5:
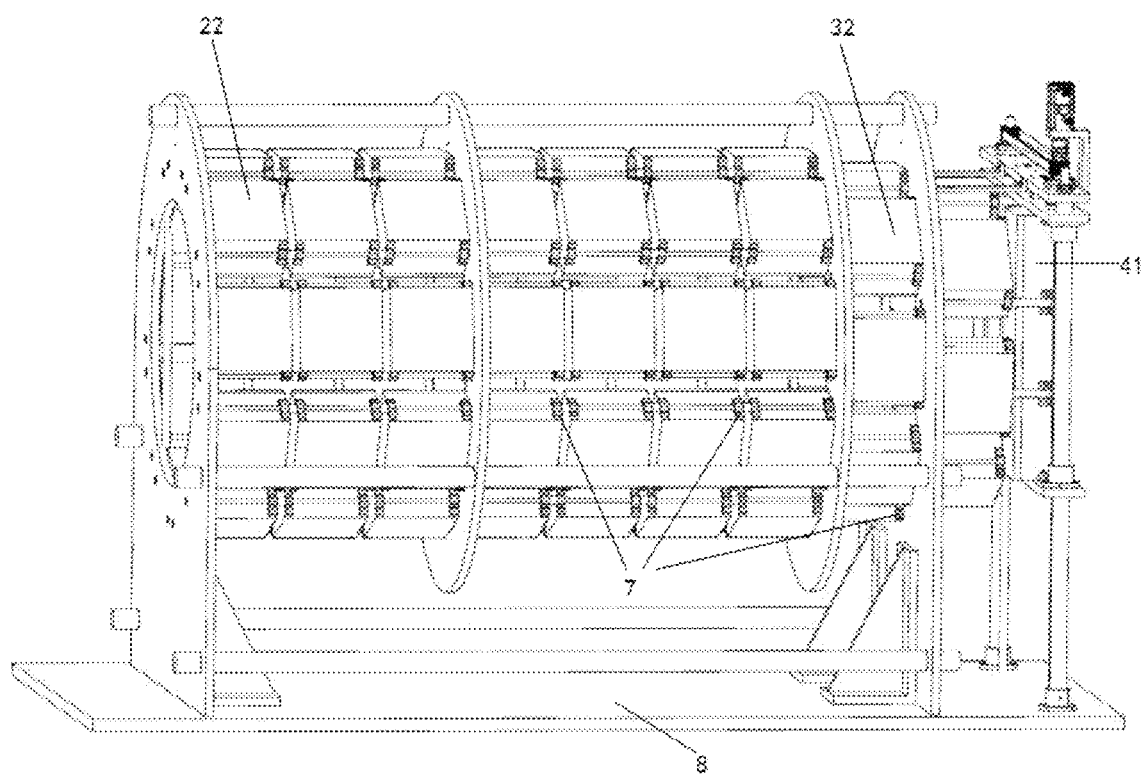
FIG. 5 is a specific configuration view of the apparatus with modules installed.

As shown in FIGS. 4 to 5, the body has a left body support plate 23 and a right body support plate 24. There are more than one support wings 6 on an inner side of a bottom of the left body support plate to help fixing, and the body has 7 body module rings that are juxtaposed. The parallel guide columns and the circumferential guide columns form an integral body guide column frame 25, and inter-column positions 26 are formed therebetween. The body PET detection modules are installed in the inter-column positions 26. Due to a large span, a body intermediate support frame 27 is arranged between the third and fourth body module rings for reinforcement, and three support columns 28 evenly penetrate outside the body guide column frame for reinforcement. For economical consideration, the right body support plate is not provided with a bottom, and the support effect of the bottom is implemented by a head intermediate support plate. The head module rings are divided into two stages. Since the head intermediate support plate 33 can have already fixed the head module rings of the second stage, and the function of the left head support plate is implemented by the right body support plate, in fact, the two are combined into one; the right head support plate is also not provided, and the head has a head guide column 34.

The top is integrally hoisted under a second plate 462, and the second plate is moved up and down by a lead screw driven by a motor. The second plate 462 is parallel with a first plate 461, and both the first plate and the second plate are horizontal. The first plate is fixed by a vertical front support column 463 and a vertical rear support column 464. There is a front lead screw on an inner side of the front support column, and the front lead screw is invisible in the figure. There is a rear lead screw 465 on an inner side of the rear support column. An upper end of the front lead screw is connected to a shaft of the motor, and an upper end of the rear lead screw is connected to a synchronous pulley. Lower ends of the front lead screw and the rear lead screw are fixed on a rotatable seat on a bottom plate 8. The second plate has a front nut seat and a rear nut seat respectively. The front nut seat cooperates with the front lead screw in an embedding manner, and the rear nut seat cooperates with the rear lead screw in an embedding manner. The shaft of the motor is provided with a motor shaft bushing 45, and a synchronous belt 43 is sleeved over the synchronous pulley 42 and the motor shaft bushing 45 in a tensioned state, so that the shaft of the motor and the synchronous pulley rotate synchronously, thereby driving the front lead screw and the rear lead screw to rotate synchronously, so that the second plate ascends or descends. A base 8 enables the body, the head and the top to be fixed collectively, thus avoiding relative displacement.

In addition, an insulating ring or the like may be installed between each detection module and the guide column or the support plate, which can ensure that each module receives a signal relatively independently.

Eighth Embodiment

The specific configuration of the detection modules is defined. The detection modules can adopt the general configuration in the art, or can be commercially purchased as a whole, or can be configured according to the following manner the body PET detection module, the head PET detection module and the top PET detection module are all PET detection modules of uniform specifications, and all have a square or rectangular detection surface, preferably square; and each PET detection module is composed of a PET detection crystal, a light guide and a photosensor array arranged in sequence. A coincidence circuit is connected between every two PET detection modules, so that each occurring LOR can be detected; a material of the PET detection crystal is a scintillation crystal, and the scintillation crystal consists of a crystal strip array composed of a plurality of crystal strips or consists of one or more integrally cut crystal. Each PET detection module is specifically configured such that the light guide is tightly coupled to both the photosensor array and the PET detection crystal. This tight coupling is substantially free of gaps.

Preferably, the material of the scintillation crystal is selected from one or more of bismuth germanate (BGO) crystal, sodium iodide (NaI) crystal, NaI (Tl) single crystal, lutetium silicate (LSO) crystal, gadolinium silicate (GSO) crystal and yttrium lutetium silicate (LYSO). Broadly, all the commercially available crystals can be used herein. A spacer made of a high atomic number material is installed between all the detection module rings, or a spacer made of a high atomic number material is installed between some of the detection module rings; the high atomic number material is lead or tungsten. The crystal strip array is composed of a plurality of crystal strips; and each of the one or more crystal blocks is composed of one or more integrally cut crystal.

Ninth Embodiment

Generally speaking, the above PET apparatus in which the body, the head and the top cooperate with each other is sufficient for detection, because the leg or foot is generally less concerned in PET detection. However, for special needs, the above PET apparatus may also be designed to be a fully enclosed detection device similar to the capsule type. For example, it includes the aforementioned whole-body PET device with a gradually narrowed head, and further includes a bottom; the bottom, the body, the head and the top are closely arranged in sequence; and the bottom is composed of a plurality of bottom PET detection modules. Detection surfaces of the plurality of bottom PET detection modules are located in the same plane or approximately in the same plane, the bottom is located on the other side of the body opposite to the head, and the bottom can move under the action of a mechanical device to avoid the opening of the body. Herein, the bottom may be a collection of planar or nearly planar detection modules similar to the top, but the detection area is much larger than that of the top since the larger opening on the other side of the body has to be taken care of.

Tenth Embodiment

On the basis of the ninth embodiment, if it is desired to further reduce the number of modules, since the space required by the foot is generally not large, an apparatus rear end for detecting the foot can be made the same as or similar to the aforementioned head and top. Specifically, it includes the aforementioned whole-body PET device with a gradually narrowed head, and further includes a bottom and a tail; the bottom is composed of a plurality of bottom PET detection modules, and the tail is composed of M tail module rings, where M is a natural number and the number is at least 2. Among the M tail module rings, a size of the rings decreases in sequence from a first tail module ring to a $M^{th}$ tail module ring, and the M tail module rings are closely arranged in the axial direction in the order from the first tail module ring to the $M^{th}$ tail module ring to form the tail. Detection surfaces of the plurality of bottom PET detection modules are located in the same plane or approximately in the same plane, and the bottom is located on the other side of the body opposite to the head; the bottom and the tail are integrally fixed, and can move under the action of a mechanical device to avoid the opening of the body.

Eleventh Embodiment

On the basis of the apparatus of the present disclosure, two aforementioned whole-body PET devices may also be directly arranged symmetrically with the openings of the bodies facing each other, and a detection object or a human body phantom can be placed in the openings, so that a fully enclosed whole-body detection can be directly realized. Specifically, it includes the aforementioned whole-body PET device with a gradually narrowed head, and further includes a second whole-body PET device arranged mirror-symmetrical with the whole-body PET device; the whole-body PET device has a second body, a second head and a second top that are mirror-symmetrical with the body, the head and the top respectively; the second body, the second head and the second top are closely arranged in sequence, and the opening of the body and a second opening of the second body can move within a range of 10 cm. It is important to note that the coincidence circuits of the two whole-body PET devices are combined together.

Described above are only specific embodiments of the present disclosure, but the scope of protection of the present disclosure is not limited thereto. Any change or replacement that can be conceived without creative efforts shall be covered within the scope of protection of the present disclosure. Therefore, the scope of protection of the present disclosure shall be subject to the scope of protection of the claims.

The invention claimed is:

1. A whole-body PET device with a gradually narrowed head, comprising:
a body, a head and a top that are arranged in sequence;
wherein the body is composed of a plurality of body module rings, the head is composed of N head module rings, and the top is composed of a plurality of top PET detection modules; where N is a natural number and the number is at least 2;
each of the body module rings is composed of several body PET detection modules evenly distributed in a circumferential direction, and a detection surface of each body PET detection module is arranged facing an interior of the body; all the body module rings are arranged in an axial direction to form the body;
among the N head module rings, a size of the rings decreases in sequence from a first head module ring to a $N^{th}$ head module ring, and the N head module rings are arranged in the axial direction in the order from the first head module ring to the $N^{th}$ head module ring to form the head; each of the N head module rings is composed of several head PET detection modules; and
detection surfaces of the plurality of top PET detection modules are located in the same plane or approximately in the same plane, and the detection surfaces of all the top PET detection modules are oriented in a direction toward the head or the body,
wherein:
the installation of the body is implemented using a first support method or a second support method;
in the first support method, the body is installed between a left body support plate and a right body support plate, and a body guide column frame is installed between the left body support plate and the right body support plate; for the body guide column frame, several lateral horizontal guide columns and approximately circular guide columns connected end to end in a vertical plane are arranged cross each other to form an overall hollow cylindrical body guide column frame and several inter-column positions suitable for installation of body PET modules, and each body PET detection module is installed in the inter-column position;

in the second support method, the body is installed between a left body support plate and a right body support plate, and a body guide column frame is installed between the left body support plate and the right body support plate; for the body guide column frame, several lateral horizontal guide columns and approximately circular guide column loops connected end to end in a vertical plane are arranged cross each other to form an overall hollow cylindrical body guide column frame and several inter-column positions suitable for installation of body PET modules, and each body PET detection module is installed in the inter-column position; and at least one of the guide column loops is replaced by a body intermediate support plate;

the installation of the head is implemented using a third support method or a fourth support method;

in the third support method, the head is installed between a left head support plate and a right head support plate; the first head module ring is installed between the left head support plate and a first head intermediate support plate, a $M^{th}$ head module ring is installed between a (M−1)th head intermediate support plate and a $M^{th}$ head intermediate support plate, where 2≤M≤N−1 and M is an integer, and the $N^{th}$ head module ring is installed between a $(N−1)^{th}$ head intermediate support plate and the right head support plate; each head PET detection module is installed on two adjacent head guide columns, and each of the head guide columns is parallel to an axis of the head;

in the fourth support method, a right side of a $M^{th}$ head module ring is perpendicularly installed on a $M^{th}$ head intermediate support plate, where 1≤M≤N−1 and M is an integer, and a left side of the $N^{th}$ head module ring is installed on a $(N−1)^{th}$ head intermediate support plate; each head PET detection module is installed on two adjacent head guide columns, and each of the head guide columns is parallel to an axis of the head;

the installation of the top is implemented using a fifth support method or a sixth support method;

in the fifth support method, the top is fixed on one surface of a vertically arranged top support plate;

in the sixth support method, the top is fixed on a second plate, and the second plate is embedded with a nut seat which cooperates with a lead screw driven by a motor, so that the top can be moved in parallel when driven by the motor; and except for the top support plate, all the other support plates have circular or approximately circular through holes.

2. The whole-body PET device with a gradually narrowed head according to claim 1, wherein:

the number of N is one of the integers of 2-5;

the number of PET detection modules on the $N^{th}$ head module ring is 1-5 smaller than the number of PET detection modules on a $(N−1)^{th}$ head module ring, and the number of PET detection modules on the first head module ring is 1-5 smaller than the number of PET detection modules on the body module ring;

at least 85% of the area of an outer opening portion of the $N^{th}$ head module ring is covered by the top; and the PET device further comprises a tail, and the tail is composed of a plurality of tail PET detection modules; detection surfaces of the plurality of tail PET detection modules are located in the same plane or approximately in the same plane, and the detection surfaces of all the tail PET detection modules are oriented in a direction toward the head or the body.

3. The whole-body PET device with a gradually narrowed head according to claim 2, wherein:

the number of N is 2;

the number of head PET detection modules on a second head module ring is 1-2 smaller than the number of head PET detection modules on the first head module ring; the number of PET detection modules on the first head module ring is 1-2 smaller than the PET detection modules on the body module ring; and at least 90% of the area of the outer opening portion of the $N^{th}$ head module ring is covered by the top.

4. The whole-body PET device with a gradually narrowed head according to claim 1, wherein:

both the left body support plate and the right body support plate have a bottom support portion, and the body intermediate support plates have a bottom support portion, or are supported by several support columns penetrating the left body support plate, the right body support plate and all the body intermediate support plates;

both the left head support plate and the right head support plate have a bottom support portion, and the head intermediate support plates have a bottom support portion, or are supported by several support columns penetrating the left head support plate, the right head support plate and all the head intermediate support plates; and the top support plate has a bottom support portion, and a shaft bushing of the motor is embedded and fixed on a first plate.

5. The whole-body PET device with a gradually narrowed head according to claim 4, wherein:

the body PET detection modules, the head PET detection modules and the top PET detection modules are all PET detection modules of uniform specifications, and all have a square or rectangular detection surface; and each PET detection module is composed of a PET detection crystal, a light guide and a photosensor array arranged in sequence; and a coincidence circuit is connected between every two PET detection modules; a material of the PET detection crystal is a scintillation crystal, and the scintillation crystal consists of a crystal strip array composed of a plurality of crystal strips or consists of one or more integrally cut crystal.

6. The whole-body PET device with a gradually narrowed head according to claim 5, wherein:

each PET detection module is specifically configured such that the light guide is tightly coupled to both the photosensor array and the PET detection crystal;

the material of the scintillation crystal is selected from one or more of bismuth germanate (BGO) crystal, sodium iodide (NaI) crystal, NaI (TI) single crystal, lutetium silicate (LSO) crystal, gadolinium silicate (GSO) crystal and yttrium lutetium silicate (LYSO);

a spacer made of a high atomic number material is installed between all the detection module rings, or a spacer made of a high atomic number material is installed between some of the detection module rings; the high atomic number material is lead or tungsten; and the crystal strip array is composed of a plurality of crystal strips; and each of the one or more crystal blocks is composed of one or more integrally cut crystal.

7. The whole-body PET device with a gradually narrowed head according to claim 1, wherein:

the body PET detection modules, the head PET detection modules and the top PET detection modules are all PET detection modules of uniform specifications, and all have a square or rectangular detection surface; and each PET detection module is composed of a PET detection crystal, a light guide and a photosensor array arranged in sequence; and a coincidence circuit is connected between every two PET detection modules; a material of the PET detection crystal is a scintillation crystal, and the scintillation crystal consists of a crystal strip array composed of a plurality of crystal strips or consists of one or more integrally cut crystal.

8. The whole-body PET device with a gradually narrowed head according to claim 7, wherein:

each PET detection module is specifically configured such that the light guide is tightly coupled to both the photosensor array and the PET detection crystal;

the material of the scintillation crystal is selected from one or more of bismuth germanate (BGO) crystal, sodium iodide (NaI) crystal, NaI (TI) single crystal, lutetium silicate (LSO) crystal, gadolinium silicate (GSO) crystal and yttrium lutetium silicate (LYSO);

a spacer made of a high atomic number material is installed between all the detection module rings, or a spacer made of a high atomic number material is installed between some of the detection module rings; the high atomic number material is lead or tungsten; and the crystal strip array is composed of a plurality of crystal strips; and each of the one or more crystal blocks is composed of one or more integrally cut crystal.

9. A whole-body PET combined device with a gradually narrowed head, comprising the whole-body PET device with a gradually narrowed head according to claim 1, and further comprising a bottom; wherein the bottom, the body, the head and the top are arranged in sequence, and the bottom is composed of a plurality of bottom PET detection modules; and detection surfaces of the plurality of bottom PET detection modules are located in the same plane or approximately in the same plane, the bottom is located on the other side of the body opposite to the head, and the bottom can move under the action of a mechanical device to avoid an opening of the body.

10. A whole-body PET combined device with a gradually narrowed head, comprising the whole-body PET device with a gradually narrowed head according to claim 1, and further comprising a bottom and a tail; wherein the bottom is composed of a plurality of bottom PET detection modules, and the tail is composed of M tail module rings, where M is a natural number and the number is at least 2;

among the M tail module rings, a size of the rings decreases in sequence from a first tail module ring to a $M^{th}$ tail module ring, and the M tail module rings are arranged in the axial direction in the order from the first tail module ring to the $M^{th}$ tail module ring to form the tail; and detection surfaces of the plurality of bottom PET detection modules are located in the same plane or approximately in the same plane, and the bottom is located on the other side of the body opposite to the head; the bottom and the tail are integrally fixed, and can move under the action of a mechanical device to avoid an opening of the body.

11. A whole-body PET combined device with a gradually narrowed head, comprising the whole-body PET device with a gradually narrowed head according to claim 1, and further comprising a second whole-body PET device arranged mirror-symmetrical with the whole-body PET device; wherein the whole-body PET device has a second body, a second head and a second top that are mirror-symmetrical with the body, the head and the top respectively; the second body, the second head and the second top are arranged in sequence, and an opening of the body and a second opening of the second body can move within a range of 10 cm.

* * * * *